United States Patent [19]

Hanna

[11] Patent Number: 4,873,979
[45] Date of Patent: Oct. 17, 1989

[54] MICRO-SURGICAL INSTRUMENT FOR USE AS GRIPPER OF SCISSORS

[76] Inventor: Khalil Hanna, 19 rue Las Cases, 75007 Paris, France

[21] Appl. No.: 128,074
[22] PCT Filed: Mar. 18, 1987
[86] PCT No.: PCT/FR87/00078
  § 371 Date: Nov. 17, 1987
  § 102(e) Date: Nov. 17, 1987
[87] PCT Pub. No.: WO87/05484
  PCT Pub. Date: Sep. 24, 1987

[30] Foreign Application Priority Data

Mar. 18, 1986 [FR] France .................. 86 03828

[51] Int. Cl.⁴ ........................... A61B 17/30
[52] U.S. Cl. ........................... 128/354; 128/321
[58] Field of Search ............ 128/303 R, 318, 321–324, 128/326, 346, 354

[56] References Cited

U.S. PATENT DOCUMENTS

| | | | |
|---|---|---|---|
| 4,198,980 | 4/1980 | Clark | 128/303 R |
| 4,212,305 | 7/1980 | Lahay | 128/321 |
| 4,248,233 | 2/1981 | von Zeppelin et al. | 128/323 |
| 4,318,313 | 3/1982 | Tartaglia | 128/354 |
| 4,442,837 | 4/1984 | Keatley | 128/354 |
| 4,446,866 | 5/1984 | Davison | 128/321 |
| 4,452,106 | 6/1984 | Tartaglia | 128/354 |
| 4,506,669 | 3/1985 | Blake | 128/354 |

Primary Examiner—Max Hindenburg
Attorney, Agent, or Firm—Fleit, Jacobson, Cohn, Price, Holman & Stern

[57] ABSTRACT

The present invention concerns a microsurgical instrument for use as pincers or scissors.

This instrument comprises two rigid longitudinal arms (1 and 2) mutually pivoted about a transverse axis (7) at their respective proximal ends (5, 6) so that their respective distal ends (22 and 23) are adapted to co-operate in a pinching or cutting action; the arms (1 and 2) having respective manual operation zones (8 and 9) between the pivot axis (7) and their respective distal ends (22 and 23) as well as means for resilient urging of the arms (1 and 2) in relative rotation in a direction of mutual spacing of their distal ends (22 and 23).

Application to the production of pincers or scissors of great precision, for example for use as a needle-holder, as pincers with or without claws, as scissors for corneal grafting or as scissors with other uses.

33 Claims, 5 Drawing Sheets

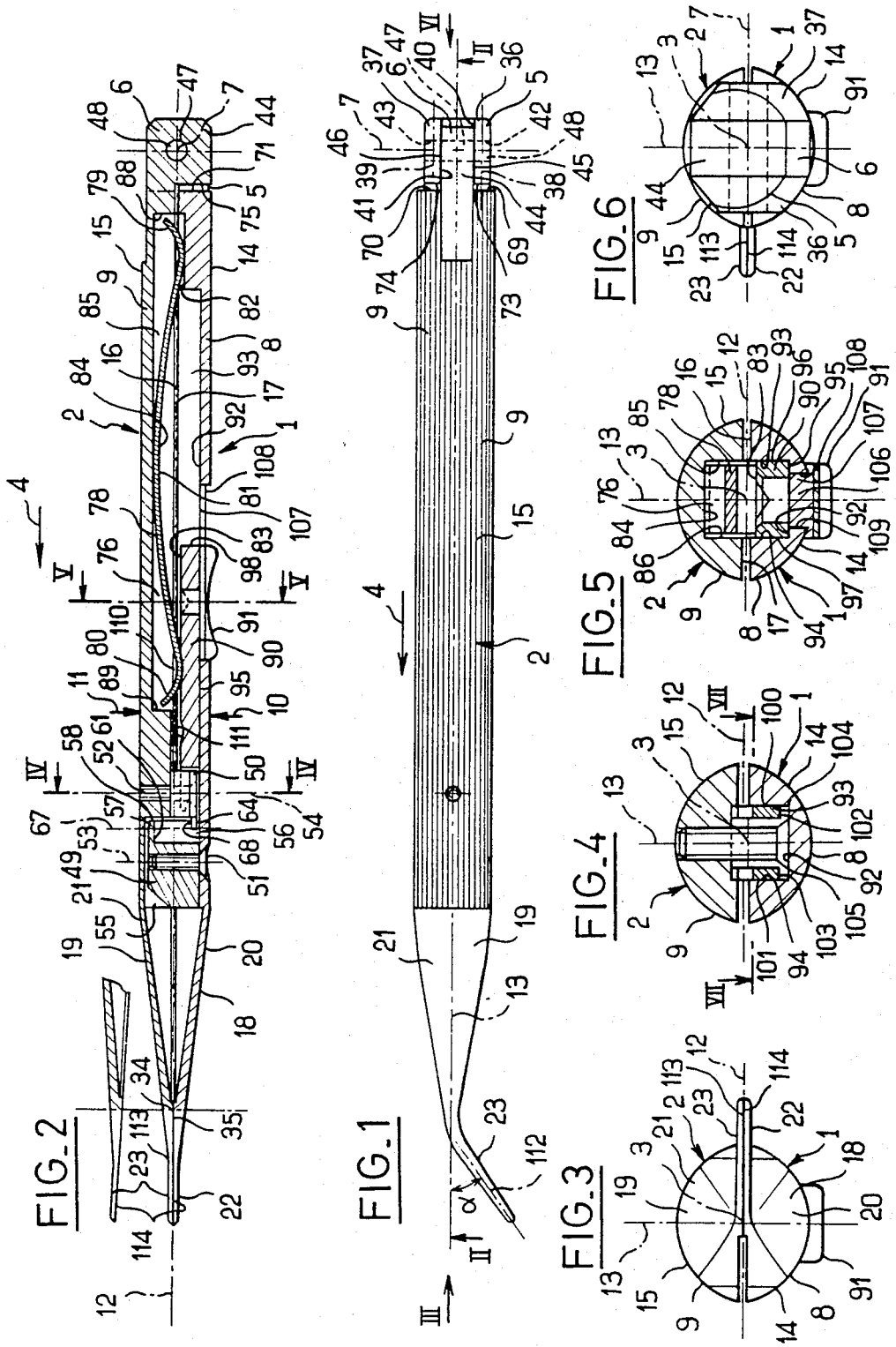

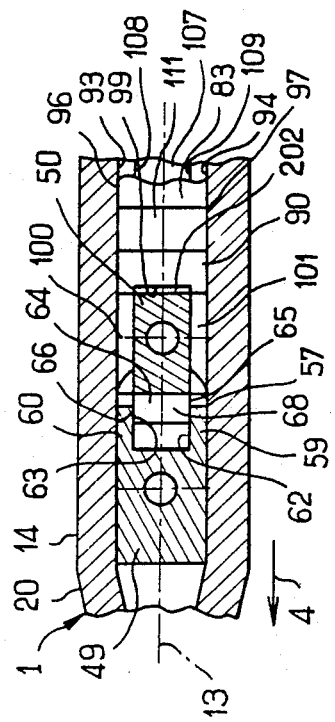
FIG_7
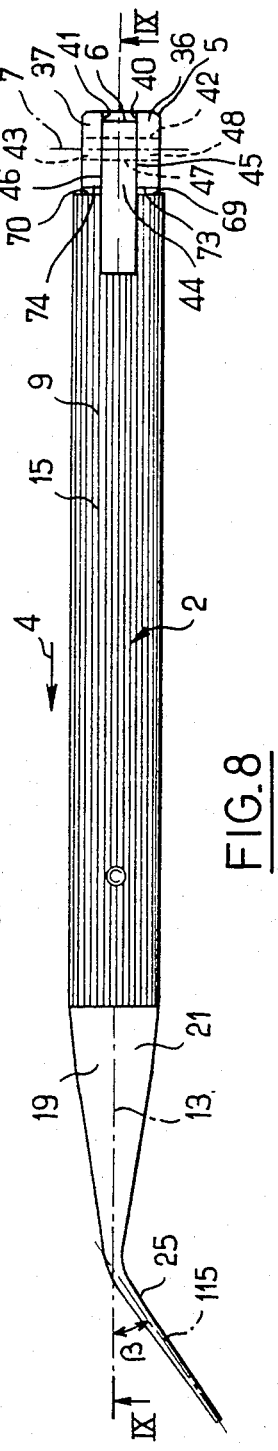
FIG.8
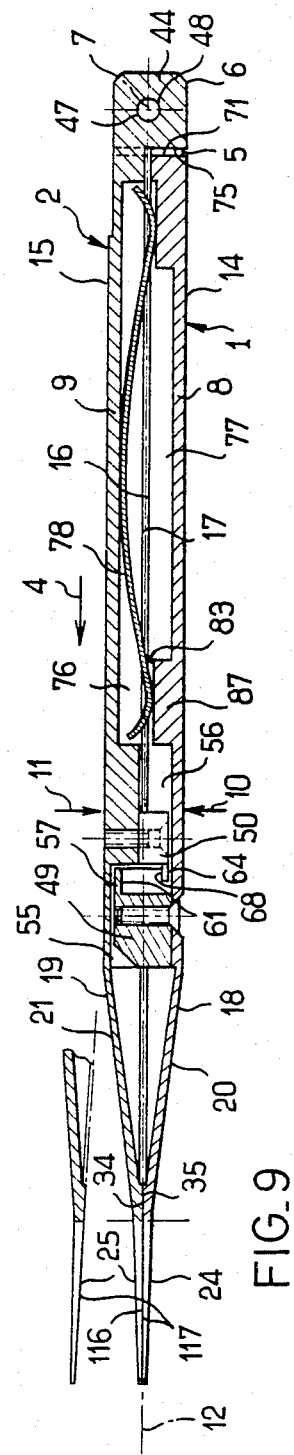
FIG_9

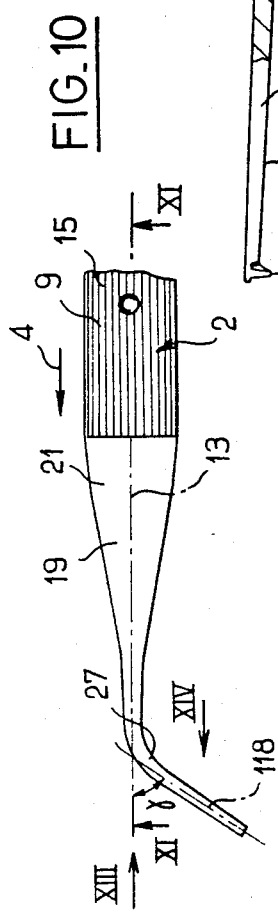
FIG.10
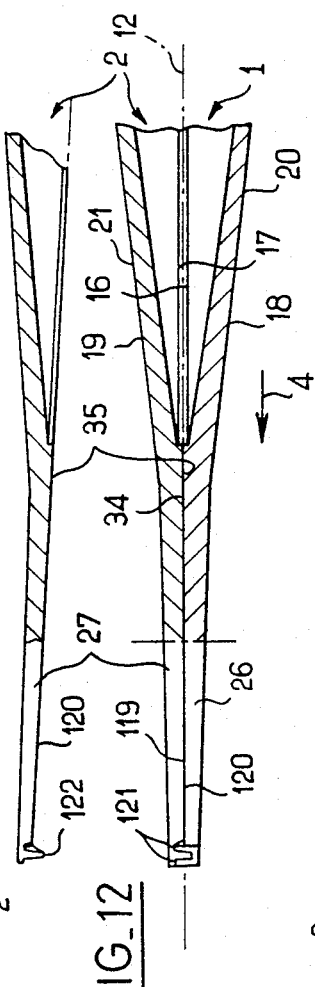
FIG.12
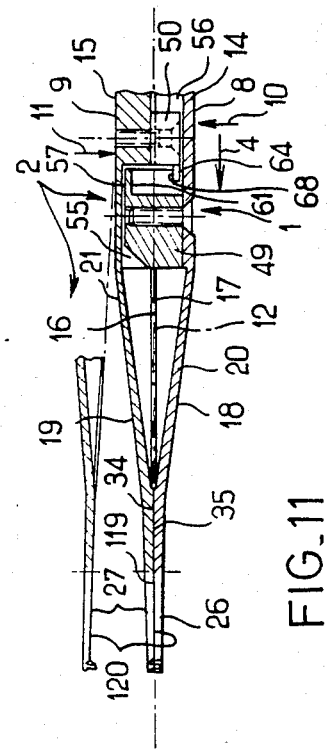
FIG.11
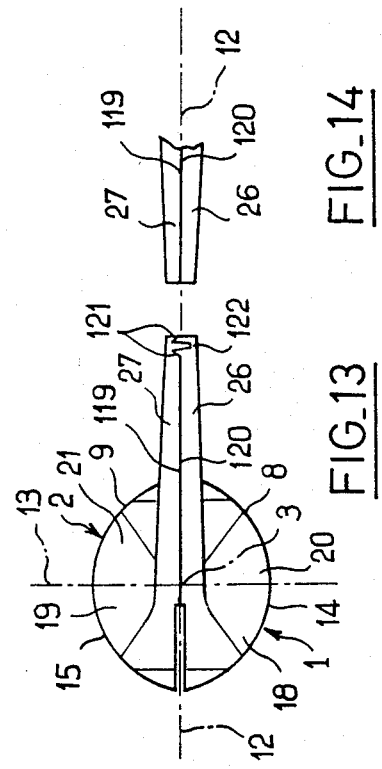
FIG.13
FIG.14

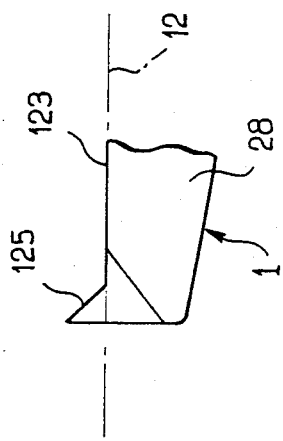
FIG_18
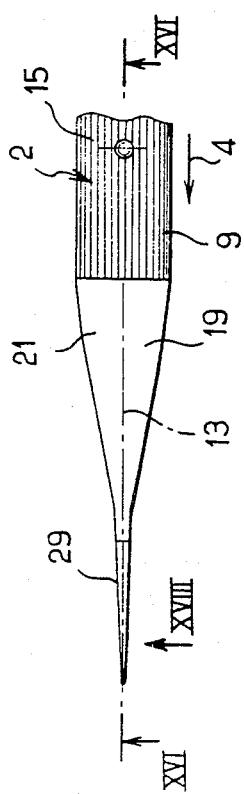
FIG_15
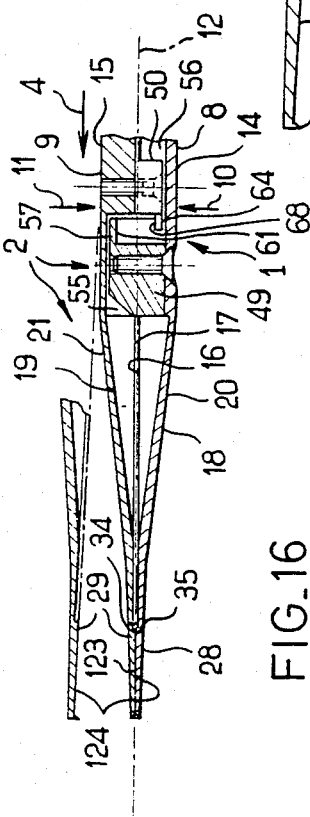
FIG_16
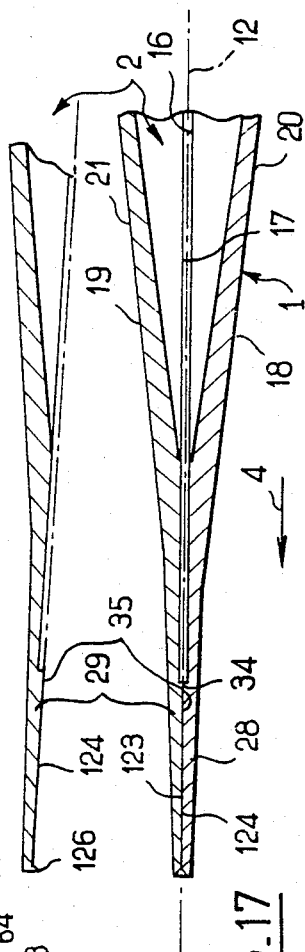
FIG_17

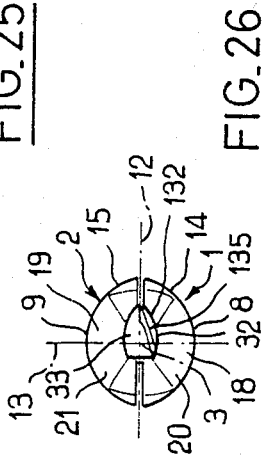
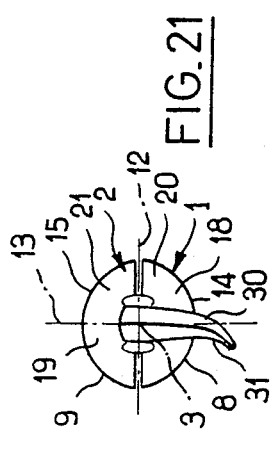
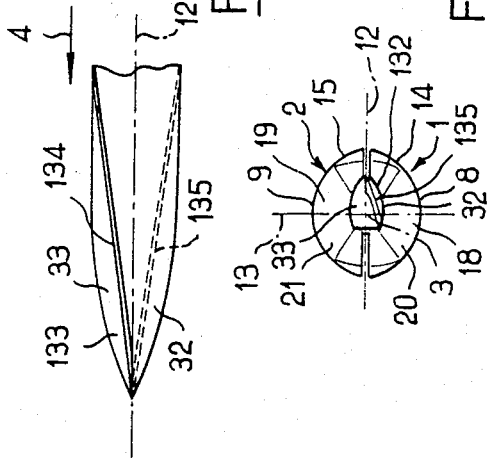
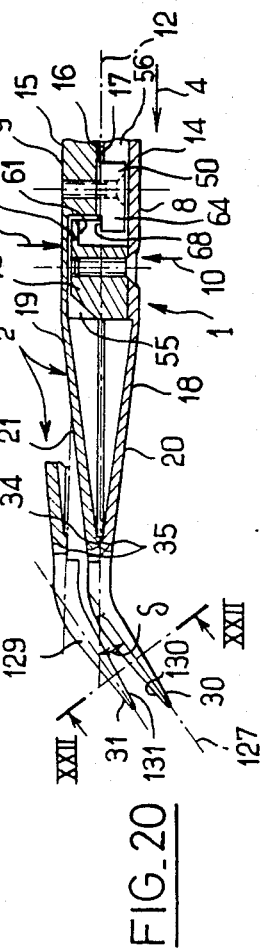
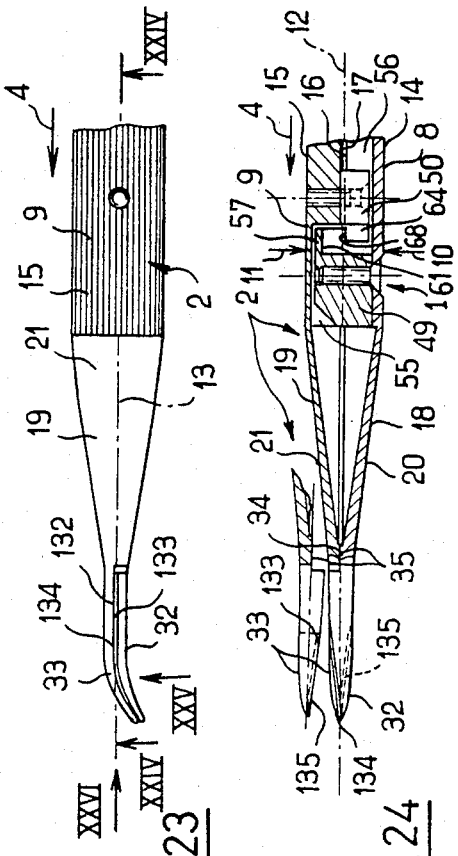

MICRO-SURGICAL INSTRUMENT FOR USE AS GRIPPER OF SCISSORS

The present invention relates to a microsurgical instrument for use as pincers or scissors.

More precisely, it relates to such an instrument of the type comprising two rigid longitudinal arms which are mutually pivoted about a defined transverse axis and having on the one hand respective proximal ends and on the other hand respective distal ends, the said distal ends being longitudinally spaced with respect to the said axis and adapted to co-operate in a pinching or cutting action, respectively, by relative rotation of the two arms about the said axis in a first direction corresponding to a mutual approach of the said distal ends, the arms having respective manual operation zones for relative rotation about the said axis in the said first direction whilst there is provided means for resilient urging the arms in relative rotation about the said axis in a second direction opposite from the said first direction and corresponding to a mutual spacing of the said distal ends.

In the presently known manner of production, instruments of this type are characterised by the fact that the transverse axis for mutual pivoting of the two rigid longitudinal arms is situated between the proximal ends and the distal ends, generally nearer to the distal ends than the proximal ends; the manual operation zones of the arms are then situated at the proximal ends, and the resilient urging means for the arms are constituted by two leaf springs of which each extends approximately longitudinally of a respective arm, with which it is rigid at the proximal end of this; the two blades being curved the one towards the other from the proximal ends of the arms and pivoting the one on the other at a certain distance from these proximal ends.

Such a structure has a certain number of inconveniences resulting from the proximity of the mutual pivot axis of the arms to the distal ends of these latter.

If the instrument is a needle-holder, that is to say a pincers intended for the manipulation of a needle carrying a suture, this proximity brings about a significant risk of catching of the suture in the pivot, that is to say breaking of the suture which is very weak.

If the instrument is a pair of scissors, of which the arms have at their distal ends the form of blades able to co-operate in a cutting action by mutual crossing, the closeness of the pivot axis and the blades complicates the geometry of these latter.

Further, as the instrument is conceived either as a pincers or as a pair of scissors, the proximity of the pivot axis with respect to the distal ends of the arms necessarily associates with a predetermined mutual spacing of these distal ends a relatively large angular opening between the two arms.

There results on the one hand that the movement of the arms in the first direction, that is to say in the direction of mutual approach of the distal ends, is translated by a tendency of these latter to move longitudinally whatever finds itself between them, which is a needle if the instrument is a needle-holding pincers, a muscle or tissue if the instrument is a pincers or pair of scissors, which interferes with the precision of the operation, which can be crucial in the field of microsurgery.

There results on the other hand that a determined mutual spacing of the distal ends of the arms corresponds to a much more significant spacing of the proximal ends of these arms, when these proximal ends are further extended from the pivot axis than the distal ends; so that, for a determined amplitude of movement of mutual approach or mutual spacing of the distal ends there corresponds a much more significant amplitude of movement of mutual approach or mutual spacing of the proximal ends where the manual operation zones of the arms are situated; there results a significant encumbering of the instrument in the hand of the surgeon, which is translated by a certain discomfort of use and by a difficulty of control with precision of the relative positions of the distal ends of the arms; further, it is noted that this significant encumbering in the hand of the surgeon is positioned in a plane perpendicular to the pivot axis, so that the instrument has parallel to this axis much reduced dimensions, such that it is difficult for the surgeon to turn the instrument on itself in his hand, and he is obliged to turn his whole hand with the instrument when a rotation of this on itself is desired.

This inconvenience is aggravated by the fact that the resilient urging means for the arms are made in the form of the two mentioned leaf springs; in effect, for limiting the longitudinal encumbrance of the instrument, it is provided that the two leaf springs are positioned in the hand of the surgeon as well as the manual operating zones of the arms; now, for ensuring their functioning, the leaf springs are oriented so that they have perpendicularly to a plane perpendicular to the pivot axis of the arms their most extended surfaces, which ensures wedging of the instrument in the hand; it is generally considered that this wedging is inconvenient because it becomes practically impossible to turn the instrument on itself in the hand, even if the possibility of a closed gripping of the instrument is otherwise desirable.

The object of the present invention is to propose, for a microsurgical instrument for use as pincers or as scissors of the type indicated above, a structure permitting the remedying of all these inconveniences.

For this, the present invention proposes an instrument of the type indicated above, characterised in that the said transverse axis of mutual pivoting of the arms is situated at the proximal ends of these latter, and in that the said manual operation zones of the arms are situated between the said axis and distal ends of the arms.

It can be noted that there has already been proposed, for use in microsurgery, pincers of the BRUCELLES type, having two resiliently deformable longitudinal arms, mutually fixed the one to the other at their ends; such pincers can only have the same uses as the instruments of the type envisaged by the present invention, on account of the inherent suppleness of their arms and because of the absence of a defined axis of relative rotation of these latter, which completely excludes use supposing the application of relatively significant forces by the distal ends of the arms and a use necessitating a precise control of the relative positions of these distal ends; in particular, the production of scissors by means of such a structure appears excluded.

On the contrary, by conserving a materially defined axis, for example by a pivot pin, by way of mutual pivoting of the arms and by conserving to these latter as good a rigidity as possible, the present invention proposes a high precision structure applicable to these instruments, which are able further to apply significant forces at their distal ends.

To these advantages, the structure of the invention adds a maximum spacing of the pivot axis of these arms with respect to the distal ends of these latter, that is to say the elimination of any risk of catching of the suture if the instrument is made as a needle-holding pincers and the possibility of providing cutting blades of a comparatively more simple geometric shape if scissors are to be produced.

Further, the proximity of the manual operation zones of the arms with respect to the distal ends of these latter permits better controlling of the relative position of these latter and the considerable reduction of the encumbrance of the instrument in the hand of the surgeon; in particular, the instrument can have similar dimensions in any transverse direction, as the distal ends are mutually spaced to the maximum or mutually closed to the maximum, which considerably facilitates the gripping of the instrument by the surgeon and permits a rotation of the instrument on itself in his hand in a manner particularly convenient, flexible and regular; in fact, the orientation of the instrument about a longitudinal direction in the hand becomes practically indifferent, which brings about a particularly great flexibility of use of the instrument.

According to a preferred embodiment of the instrument according to the invention, the resilient urging means for the arms comprises at least one compression spring interposed between the arms, between the said axis and the said distal ends; for example, the resilient urging means comprises at least one approximately longitudinal leaf spring, curved in a median plane perpendicular to the axis and having two end zones in abutment against one of the arms in respective circumferential directions centered on the said axis and an intermediate zone in abutment against the other arm in a circumferential direction centered on the said axis, between the said axis and the said distal ends.

Then, the resilient urging means constitute no hindrance to the free manipulation of the instrument, whatever their stiffness.

For certain applications, the instrument according to the invention can comprise means for immobilising, at will, the two arms against a relative rotation about the said axis in the said second direction, in a relative position of maximum mutual approach of the said distal ends; then, advantageously, these immobilisation means can comprise, between the said axis and the said distal ends, on the one hand a catch fixed to one of the arms and on the other hand a bolt longitudinally slidingly mounted on the other arm and manually accessible in the manual operation zone of this arm for being moved at will into a position of engagement with the catch, for providing the said immobilisation, or into a position of disengagement with respect to the catch, for removing the said immobilisation; when the resilient urging means for the arms comprise a leaf spring arranged as previously indicated, this leaf spring advantageously abuts via the intermediary of the bolt on the arm carrying this bolt, which permits ensuring in a particularly convenient manner and under a reduced encumbrance a ratchet motion of the bolt into its respective positions of engagement and disengagement with the catch, against any accidental longitudinal sliding.

Advantageously, means are provided for limiting the mutual spacing of the distal ends of the arms, as well as means for mutual guiding of the arms in relative rotation about their mutual pivot axis without possibility of relative translation parallel to this; advantageously, these means of limiting the mutual spacing of the distal ends of the arms and these means of mutual guiding of the arms in relative rotation are defined by different surfaces of transverse projections which the two arms rigidly present the one towards the other, in respective circumferential directions centered on the mutual pivot axis, between this axis and their distal ends and preferably nearer to the distal ends than to the axis; if a bolt is provided as indicated above, one of these projections advantageously constitutes the catch of this bolt.

Thus, it is possible to arrange a particularly complete instrument and bring this about with a small number of pieces, which permits its production with reduced encumbrance and at low cost.

Further, it will be understood that the entire mechanism of the instrument can be concealed between the arms of it, so that it is possible to give to this instrument simple and functional aesthetics, which can be invariable from an instrument for use as pincers, whatever the type of pincers, to an instrument for use as scissors, whatever the use of these scissors, if one naturally excepts the shape of the distal ends of the arms, which is adapted to the function of the instrument; thus, thanks to the recommended structure of the present invention, it becomes possible to produce a homogenously aesthetic range of instruments adapted to different functions without reducing at all the functional qualities of these instruments.

Other characteristics and advantages of the invention will appear from the following description, relating to several non-limitative embodiments, as well as the accompanying drawings which form an integral part of this description.

FIG. 1 shows a side view of a needle-carrier according to the invention.

FIG. 2 shows a view of this needle-carrier partly in section on a median longitudinal plane, perpendicular to the axis of mutual pivoting of the two arms of the needle-carrier shown by II—II in FIG. 1.

FIG. 3 shows a view of the needle-carrier in the direction of the longitudinal arrow III of FIG. 1.

FIGS. 4 and 5 show a view of the needle-carrier in section on transverse planes IV—IV and V—V respectively in FIG. 2.

FIG. 6 shows a view of the needle-carrier in the longitudinal direction shown by the arrow VI in FIG. 1, opposite to the direction of the arrow III.

FIG. 7 shows a view of the needle-carrier in cross-section on a longitudinal plane parallel to the mutual pivot axis of the two arms and shown by VII—VII in FIG. 4.

FIG. 8 shows a side view of flat, bent-nosed pincers, according to the invention.

FIG. 9 shows a view of these pincers essentially in section on a longitudinal median plane, perpendicular to the axis of mutual pivoting of the two arms of the pincers and shown as IX—IX in FIG. 8.

FIG. 10 shows, in a view similar to that of FIG. 8 but limited to the distal ends of the arms, a pincer for the upper right muscle made in accordance with the present invention.

FIG. 11 shows a view of the distal ends of these pincers in section on a longitudinal median plane, perpendicular to the axis (not shown) of mutual pivoting of the two arms and shown as XI—XI in FIG. 10.

FIG. 12 shows a localised enlargement of FIG. 11.

FIG. 13 shows a view of the pincers of FIG. 10 on the longitudinal arrow XIII with an enlargement greater than that of FIG. 12.

FIG. 14 shows a partial view of these pincers on the longitudinal arrow XIV, in a direction opposite to the arrow XIII, on the same scale as FIG. 13.

FIG. 15 shows, in a partial view similar to that of FIG. 10, a pincers with claws according to the present invention.

FIG. 16 shows these pincers with claws in a view similar to that of FIG. 11, that is to say in median longitudinal cross-section perpendicular to the mutual pivot axis (not shown) of the two arms of the pincers and shown as XVI—XVI in FIG. 15.

FIG. 17 shows a detail of FIG. 16 on a much larger scale.

FIG. 18 shows, in a view also on a larger scale and in the direction of arrow XVIII, parallel to the non shown axis of mutual pivoting of the arms of the pincers, a claw at the distal end of one of the arms of this latter.

FIG. 19 shows, in a partial view similar to that of FIGS. 10 and 15, scissors for grafting of the (left) cornea made in accordance with the present invention.

FIG. 20 shows, in a limited view similar to that of FIGS. 11 and 16, a view of these scissors essentially in cross-section on a median longitudinal plane perpendicular to the axis (not shown) of mutual pivoting of their arms and shown as XX—XX in FIG. 19.

FIG. 21 shows a view of these scissors in a direction of the longitudinal arrow XXI of FIG. 19.

FIG. 22 shows a view of the distal ends of the arms of these scissors in cross-section on the plane XXII—XXII in FIG. 20.

FIG. 23 shows, in a view similar to those of FIGS. 10, 15, 19 and limited to the distal ends of the arms, another pair of scissors according to the present invention.

FIG. 24 shows, in a limited view similar to that of FIGS. 11,16,20, these scissors essentially in cross-section on a median longitudinal plane perpendicular to the axis (not shown) of mutual pivoting of their arms and shown as XXIV—XXIV in FIG. 23.

FIG. 25 shows a localised enlargement of these scissors seen in the direction of the arrow XXV in FIG. 3, which arrow is parallel to the mutual pivot axis of the arms of the scissors.

FIG. 26 shows a view of the scissors in the direction of the longitudinal arrow XXVI of FIG. 23.

In all the Figures, the different instruments according to the invention are illustrated in a closed position, that is to say with the distal ends of the arms mutually approached together to the maximum; without expressly mentioned exception, the description which follows will be made with reference to this state; however, in FIGS. 2, 9, 11, 16, 20, 24, is shown in addition the distal end of the one of the respective arms in the open position, that is to say with a maximum spacing vis-a-vis the distal end of the other respective arm, supposed as to itself immobile for reasons of ease of drawing.

Further, it will be noted on examination of the assembly of the Figures that different instruments according to the invention which have been illustrated have the same external shape, if one excepts the distal ends of the arms, intended to co-operate in a pinching or cutting action and adapted to this function, so large are the analogies of structure that in the first place will be described the common points between the different instruments illustrated, before detailing the specific aspects of each.

Consequently, referring first to the entirety of FIGS. 1 to 26 where is illustrated instruments of which each comprises two arms 1 and 2 elongated in the same longitudinal direction 3 and essentially mutually juxtaposed transversely to this longitudinal direction 3; following the same longitudinal direction 4, the two arms 1 and 2 have successively:

respective end zones 5,6 which interpenetrate as will appear below and through which the arms 1 and 2 are mutually pivoted about a transverse axis 7, that is to say perpendicular to the longitudinal direction 3; compared to the overall longitudinal dimension of the arms 1 and 2, which is advantageously of the order of 12 cm but could naturally be greater or less than this value, the proximal end zones 5 and 6 of the arms 1 and 2 have a small longitudinal dimension, preferably less than 1 cm without this indication having to be considered limitative;

respective zones 8 and 9 intended for gripping of the instrument and constituting respective manual operation zones of the two arms 1 and 2 in relative rotation about the axis 7 in the direction of mutual approach of zones of these arms 1 and 2 other than their proximal end zones 5 and 6, by manual application to the two zones 8 and 9 of respective forces of opposed transverse directions 10 and 11, and more precisely approximately perpendicular to the plane 12 including the axis 7; for this, the manual operation zones 8 and 9 have a longitudinal dimension advantageously greater than half the overall longitudinal dimension of the arms, and for example of the order of ⅔ of this dimension, that is to say of the order of 7 to 8 cm in the example given above, although the figures constitute only a non-limitative indication; further, in the manual operation zones 8 and 9, the two arms 1 and 2 considered in the closed position of the instrument have together, in any transverse section plane, a constant external contour, for example circular in a manner not shown or, preferably, elliptical as on the other hand illustrated for example in FIGS. 3 to 6, 13, 21, 26; then the major axis of the ellipse is situated in the plane 12 whilst the minor axis of this ellipse is situated in a longitudinal plane 13 perpendicular to the plane 12 as well as to the axis 7 (this plane 13 is coincident with the section planes II—II, IX—IX, XI—XI, XVI—XVI, XX—XX, XXIV—XXIV); this contour of the arms 1 and 2 in their manual operation zones 8 and 9 is defined by external faces 14 and 15 which the arms 1 and 2 respectively present in these zones 8 and 9, the faces 14 and 15 being symmetrical to each other with respect to the plane 13 so that they are symmetrical to each other with respect to the plan 12 and connected along the length of this at respective plane surfaces 16 and 17 which are placed opposite each other when the instrument is in its closed position and are either disposed in the plane 12 along the length of which they are abutted, in a non-illustrated manner, or disposed in the immediate proximity of the plane 12 but withdrawn with respect to this, to which they are parallel, in a manner illustrated for example in FIGS. 2, 3 to 6, 9, 11 to 13, 16, 17, 20, 21, 24, 26; in this case, the relative spacing between the faces 16 and 17 perpendicularly to the plane 12 remains however preferably limited to a value less than 1 millimeter; for facilitating the gripping of the instrument by the manual operation zones 8 and 9 of the arms 1 and 2, the faces 14 and 15 of these latter advantageously have a covering or anti-slip treatment, in a manner known in itself; by way of non-limitative example, the transverse dimensions of the instrument in the manual operating zones 8 and 9 of the arms 1 and 2 are advantageously less than 1 cm; in the case of an elliptical section, a dimension of the order of 8 mm in the plane 12, that is to say parallel to the axis 7, has been chosen, and a dimension of the order of 7 mm perpendicular to the plane 12, the instrument being supposedly in its closed position has also been chosen, but these presently preferred figures constitute only a non-limitative indication;

respective intermediate zones 18 and 19 in which the faces 16 and 17 are continued coplanar whilst, on the contrary, the faces 14 and 15 succeed respectively, in the direction 4, conical faces 20 and 21 which converge in the direction 4 conserving a symmetry with respect to the planes 12 and 13, the instrument supposedly being in its closed position, in a manner to define a progressive external thinning of the instrument in the direction 4;

respective distal end zones which differ from one instrument to another as opposed to the previously described zones 5,6,8,9,18,19 can in themselves be identical from one instrument to the other; the respective distal end zones of the arms 1 and 2 are designated by the references 22 and 23 when they relate to the needle-holder illustrated in FIGS. 1 to 7, 24 and 25 when they relate to flat-nosed pincers illustrated in FIGS. 8 and 9, 26 and 27 when they relate to right upper muscle pincers illustrated in FIGS. 10 to 14, 28 and 29 when they relate to claw pincers illustrated in FIGS. 15 to 18, 30 and 31 when they relate to scissors illustrated in FIGS. 19 to 22, 32 and 33 when they relate to the scissors illustrated in FIGS. 23 to 26; the respective shapes of these different distal zones will be described in detail below; it will be noted however that, in a manner common to all the instruments illustrated, at the immediate proximity of the transition between the intermediate zones 18 and 19 and the mentioned distal end zones respectively succeeding to the faces 16 and 1 7, possibly disjoint when the pincers are in closed state, the plane faces 34 and 35 of the arms 1 and 2, which faces 34 and 35 are situated in respective planes including the axis 7 and coincident with the plane 12 when the instrument is closed, so that a mutual abutment of the faces 34 and 35 along the length of this plane 12 results then in the limiting of the relative pivoting of the arms 1 and 2 about the axis 7 in the direction 10, 11 of mutual approach, particularly of the respective distal ends of the two arms.

Advantageously, the respective different zones of the arms 1 and 2 which have been described are made of a single piece of material as rigid as possible, for example of treated steel, and means are provided for preventing any relative displacement of the arms parallel to the axis 7 of their mutual pivoting, so that the distal ends of the arms can be displaced the one with respect to the other only in a movement of relative rotation about the axis 7, in a manner perfectly controlled by the surgeon.

In the preferred embodiment illustrated, by way of non-limitative example, such means are provided on the one hand in the region of the respective proximal end zones 5 and 6 of the two arms 1 and 2, and on the other hand in the manual operation zones 8 and 9 of these arms, and more precisely in the immediate proximity of the transition of these zones 8 and 9 with the intermediate zones 18 and 19, respectively.

More precisely, in its proximal end zone 5, the arm 1 has the form of two flat longitudinal lugs 36 and 37, having respective median planes 38 and 39 perpendicular to the axis 7; these two lugs 36 and 37 are arranged symmetrically the one with the other with respect to the plane 13 and have the one towards the other, that is to say towards this plane, respective faces 40 and 41, mutually parallel, perpendicular to the axis 7 and symmetrical the one with the other with respect to the plane 13; it will be noted that the two lugs 36 and 37 form a projection towards the other arm 2 with respect to the face 16 of the arm 1, in such a way that the axis 7 cuts the faces 40 and 41; on the axis 7, the two lugs 36 and 37 are pierced by respective bores 42 and 43, which are circularly cylindrical about the axis 7 with the same diameter.

In its proximal end zone 6, the arm 2 has itself the form of a single longitudinal lug 44, also flat, of which the plane 13 constitutes a median plane; this lug 44 forms a projection towards the arm 1 with respect to the face 17 of the arm 2 and is cut by the axis 7; perpendicularly to this, it has in the direction of an extension with respect to the plane 13 two plane faces 45,46, mutually parallel, symmetric the one with the other with respect to the plane 13, with a mutual spacing perpendicular to this plane substantially identical to the mutual spacing of the faces 40 and 41 with which the faces 45 and 46 are respectively in contact with the possibility of relative sliding with a minimum of interference; on the axis 7, the lug 44 is pierced from one side to the other by a bore 47 circularly cylindrical about the axis 7 with a diameter identical to the respective diameters of the bores 42 and 43, and the three bores 42,47,43 thus aligned on the axis 7 receive a common pin 48, of a diameter substantially identical to the common diameter of the bores 42,47,43; this pin 48 is fixed by any appropriate means, known to the man skilled in the art, in the bore 42 and/or the bore 43, in which case it is on the contrary mounted free inside the bore 47, or the pin 48 is fixed by any means known to the man skilled in the art with the lug 44 inside the bore 47 so that it is on the contrary free with respect to the two bores 42 and 43, in such a way that this pin 48 ensures guiding of the two arms 1 and 2 in relative rotation about the axis 7 with a minimum of interference.

Naturally, other means can be provided for ensuring the guiding of the two arms 1 and 2 in relative rotation about an axis 7 perfectly defined in its position with respect to the two arms 1 and 2, in the proximal end zones 5 and 6, without departing from the scope of the present invention.

In the manual operation zones 8 and 9 of the two arms 1 and 2, and more precisely in the immediate proximity of the connection of these zones 8 and 9 with the intermediate zones 18 and 19, the means provided in the illustrated example for preventing relative movement of the two arms parallel to the axis 7 are defined by transverse projections 49 and 50 which the arms 1 and 2 present respectively towards each other, in a rigid manner but advantageously in a made up form for example by screwing as shown respectively at 51 and 52; the two projections 49 and 50 are arranged with respective median directions situated in the plane 13, circumferential and centered on the axis 7 of mutual pivoting of the arms 1 and 2, which directions are similar to rectilinear directions, respectively 53 and 54, perpendicular to the plane 12 when the instrument is closed; each of the projections 49 and 50 is symmetrical with respect to the plane 13, and the two projections are longitudinally spaced, the one with respect to the other in such a way that the projection 49, situated at the junction between the manual operation zone 8 of the arm 1 and the intermediate zone 18 of this, penetrates through the face 16 into a recess 55 which arm 2 presents opposite, hollow with respect to its face 17, in the median circumferential direction 53 of the projection 49, and the projection 50, situated between the projection 49 and the axis 7 although being nevertheless nearer the distal ends of the arms than this axis 7, penetrates through the face 17 into a recess 56 provided in the face 16 of the arm 1, in the median circumferential direction 54 of this projection 50, being of course that the instrument is considered in the closed state; the projections 49 and 50 are freely received in the respective corresponding recesses 55 and 56 for not constituting any hindrance to the relative pivoting of the arms 1 and 2 about the axis 7.

It will be noted that the recess 56 is extended longitudinally in the direction 4 further than is necessary for receiving the projection 50, and receives also, in a manner always rigid with the arm 1, the made-up piece defining the projection 49 in the preferred embodiment which is illustrated.

Towards the projection 50 in a longitudinal direction, that is to say in a direction opposite from the direction 4, the projection 49 terminates with an approximately longitudinal edge 57 having the general shape of a stirrup of which a flat zone 58 is arranged substantially perpendicularly to the plane 13, symmetrically from one side to the other of this, inside the recess 55 of the arm 2 if one supposes the instrument closed, and connects the two other flat zones 59 and 60 arranged themselves parallel to the plane 13, in respective symmetrical positions the one to the other with respect to this plane, as well as in the recess 55 of the arm 2, if one supposes the instrument closed, as in the recess 56 of the arm 1; the shape of the zones 59 and 60 of the edge 57 is more particularly visible in FIG. 8.

The zone 58 of the edge 57 has towards the plane 12, the instrument being supposed closed, a plane face 61 parallel to this plane 12 when the zones 59 and 60 of the edge 57 have towards the plane 13 respective plane faces 62 and 63 parallel to this plane 13 and symmetric the one with the other with respect to it.

Complementarily, the projection 50 presents longitudinally towards the projection 59, that is to say in the direction 4, an approximately longitudinal edge 64 arranged in the recess 56 when the instrument is closed; the edge 64 is engaged between the zones 59 and 60 of the edge 57 of the projection 49 and comes into contact with the respective faces 62 and 63 of these zones via flat faces, respectively 65 and 66, parallel to the plane 13 and turned in direction of an elongation with respect to this, with a mutual spacing of the faces 65 and 66 perpendicularly to the plane 13 substantially identical to the relative spacing of the faces 62 and 63 parallel to this plane in such a way that there is established between the face 65 and the face 62, on the one hand, and between the face 66 and the face 63 on the other hand, contacts with the possibility of relative sliding which ensures for the two arms 1 and 2, the nearest possible to their respective distal ends, an obstruction of relative displacement parallel to the axis 7 without opposing at the same time by interference the relative rotation of the two arms about this axis 7; further, opposite the face 61 of the zone 58 of the edge 57 in the circumferential direction centered on the axis 7 and similar to a direction 67 rectilinear and perpendicular to the plane 12 when the instrument is closed, the edge 64 has a plane face 68 at least approximately parallel to the plane 12 and spaced from the face 61 perpendicularly to this plane when the instrument is in a closed state whilst being able to approach the face 61 to enter in contact with it when, by relative pivoting of the arms 1 and 2 about the axis 7, in the direction of relative spacing of the zones of manual operation 8 and 9 of the arms, their intermediate zones 18 and 19 and their respective distal ends, the instrument is open; the respective faces 61 and 68 of the zone 58 of the edge 57 and of the edge 64 thus constitute abutment surfaces limiting angular opening between the arms 1 and 2 on opening of the instrument, that is to say also mutual spacing of the distal ends of the arms 1 and 2 on this opening; in FIGS. 2, 9, 11, 12, 16, 17, 20, 24, is illustrated partially the limit position as imposed on the distal end 23,25,27,29,31,33 of the arm 2 with respect to the distal end 22,24,26,28,30,32 of the arm 1 on opening of the instrument; it will be noted that the identical edges 57 and 64 of the projections 49 and 50 are found in the embodiments illustrated in all the FIGS. 1 to 18, such that the distal ends of the arms of the respectively corresponding instruments are spaced the one with respect to the other in an identical manner when these instruments are open, for example by a maximum distance, measured at the distal ends, of the order of 6 mm; this indication is in no way limitative; on the contrary, in the case of the two embodiments illustrated respectively in FIGS. 19 to 22 and FIGS. 23 to 26, corresponding to scissors, the projection 49 is identical, including its edge 57, to the projection 49 which has been described but the face 68 of the projection 50 is spaced less with respect to the face 16 of the arm 1 since it is in fact practically coplanar with this face 16; the spacing between the faces 68 and 61, perpendicular to the plane 12, when the instrument is closed is consequently small, such that the coming into mutual abutment of the faces 68 and 61 corresponds to a lesser angular displacement of the arms 1 and 2 about the axis 7, that is to say a lesser mutual spacing of the distal ends 30 and 31 or 32 and 33 of the arms 1 and 2 in the case of these two embodiments; by way of non-limitative example, the maximum value of this mutual spacing, measured at the distal ends, can be of the order of 3 mm; on the contrary, there is found in the case of these two embodiments all other arrangements already described more particularly with reference to the embodiments of FIGS. 1 to 8, and that is also found in the embodiments of FIGS. 9 to 19.

The means which have been described, intended to prevent relative movement of the arms 1 and 2 parallel to the axis 7 and to limit the angular displacement of these arms about this axis, correspond to a presently preferred embodiment; they could nevertheless be replaced by other means having the same function, without departing from the scope of the present invention; in certain cases, particularly when less precision is required, the co-operation of the faces 45 and 46 of the lug 44 of the arm 2 with the faces 40 and 41 of the lugs 36 and 37 of the arm 1 can be sufficient for preventing relative movement of the distal ends of the arms 1 and 2 parallel to the axis 7, other means for providing this is in the domain of the abilities of the man skilled in the art and can thus be provided; similarly, one can for example provide limiting of the relative angular displacement of the arms 1 and 2 to the opening of the instrument by acting not so close to the distal ends as the axis 7, as is preferred and as has been described, but close to this axis 7, for example using for this the lugs 36,37,44 which constitute for the two arms 1 and 2 respective narrowings, in a direction parallel to the axis 7; from this, in particular, the lug 44 is connected in the zone of manual operation 9 of the arm 2 via the intermediary of two faces 69 and 70 plane, coplanar, perpendicular to the plane 13 as well as to the plane 12 when the instrument is closed, and respectively arranged on one side and the other of the lug 44, similarly, between the lugs 36 and 37, connecting these latter with the manual operation zone 8, the arm 1 has a plane face 71, perpendicular to the plane 13 as well as to the plane 12 when the instrument is closed; longitudinally opposite the faces 69,70,71, respectively, the lugs 36,37,44 have respective plane faces 73,74,75 perpendicular to the plane 13 as well as to the plane 12 when the instrument is closed; the faces 73 to 75 are respectively spaced longitudinally of the faces 69 to 71 when the instrument is thus closed, but are able to approach in the respective circumferential directions so far as to bring into abutment respectively against these faces by relative warping, on relative pivoting of the arms 1 and 2 about the axis 7 in the direction of opening of instrument, that is to say a mutual spacing of its distal ends; this effect can be utilised for limiting the angular displacement of the two arms 1 and 2 on opening, in place of the co-operation between the faces 61 and 68 of the projections 49 and 50; when, on the contrary, it is not desirable to utilised such a mutual abutment of the faces 69 to 71 and of the faces 73 to 75 for limiting the angular displacement of the arms 1 and 2, as is the case in the illustrated example, there is given to the relative longitudinal spacing between the faces 69 and 73, 70 and 74, 71 and 75 when the instrument is closed a value sufficiently significant for there to be no contact established between these faces insofar as the face 68 of the edge of the projection 50 comes into contact against the face 61 of the edge of the projection 49.

It can easily be conceived that the application of manual forces in the directions indicated as 10 and 11 on the respective zones 8 and 9 of manual operation of the arms 1 and 2 permits the bringing of these latter into a position of relative closure of the instrument.

For causing opening of this are provided resilient urging means preferably constituted by at least one compression spring interposed between the arms 1 and 2 between the axis 7 of their mutual pivoting and their respective distal ends, although other methods of resilient urging of the arms can be provided without departing from the scope of the present invention.

In the illustrated example, the resilient urging means are arranged between the respective zones 8 and 9 of manual operation of the arms 1 and 2, between the axis 7 and the projection 50 the nearest to this, and are more precisely housed partly in a recess 76 which the face 17 of the arm 2 has between the projection 50 and the connection of the manual operation zone 9 with the zone of the distal end 6, and partially in a longitudinal extension of the recess 56 as far as the level of connection of the zone 8 of manual operation of the arm 1 with the proximal end zone 5 of this in the case of the embodiment of FIGS. 1 to 7, or in a recess 77 independent of the recess 56 and arranged in the face 16 between this recess 56 and the connection of the zone 8 of manual operation of the arm with the proximal end zone 5 of this in the case of the embodiment of FIGS. 8 to 26.

More precisely, in the illustrated example, the resilient urging means of the arms in the direction of opening of the instrument comprise at least one leaf spring, here unique and designated by the reference 78, arranged approximately longitudinally on a median plane coincident with the plane 13, in which it is curved in a manner to present two end zones 79 and 80 in abutment against the arm 1 respectively in the proximity of the connection of the zone 8 of manual operation of this with the proximal end zone 5 of this and in the proximity of the projection 50, and an intermediate zone 81 in abutment against the other arm 2, approximately at mid-distance, longitudinally, between the end zones 79 and 80, in the recess 76.

These abutments are brought about by the intermediary of respective generatrices of the leaf spring 78, which generatrices are parallel to the axis 7, on the respective abutment faces 82 (for the end zone 79), 83 (for the end zone 80) and 84 (for the intermediate zone 81) parallel to the plane 12 when the instrument is closed, so that the leaf spring applies thus to the arms 1 and 2, by its zones 79,80,84 opposite forces in the respective circumferential directions, centered on the axis 7.

More precisely, the abutment face 82 for the end zone 79 of the leaf spring 78 on the arm 1 is fixed with this latter, parallel to the face 16, but withdrawn with respect to this towards the interior of the extension of the recess 56 in the case of the embodiment of FIGS. 1 to 7 or towards the interior of the recess 77 in the case of the embodiments of FIGS. 8 to 26; similarly, the abutment face 84 of the intermediate zone 81 of the leaf spring 78 on the arm 2 is rigid with this latter, parallel to the face 17 of this arm, withdrawn with respect to this face 17 for constituting a bottom face of this recess 76; this bottom face 84 of the recess 76 is connected to the face 17 of the arm 2, respectively on one side and the other of the plane 13, by two plane faces 85 and 86, more particularly visible in FIG. 5, which faces 85 and 86 are parallel to the plane 13 and symmetrical to each other with respect to this and constitute for the leaf spring 78 abutments preventing this spring 78 from displacing parallel to the axis 7 with respect to the arm 2, without however constituting any hindrance to the free resilient displacement of the spring 78 in the circumferential directions centered on the axis 7; the faces 85 and 86 are in addition connected between them by the two transverse faces 88 and 89, which also connect the face 84 to the face 17 and define ends of the recess 76; longitudinally opposite the faces 88 and 89 the end zones 79 and 80 of the leaf spring 78 are curved towards the inside of the recess 76 such that the faces 88 and 89 constitute for the leaf spring 78 abutments in practice preventing any longitudinal displacement of the leaf spring 78 inside the recess 76, with respect to the arm 2 as well as with respect to the arm 1.

The abutment face 83 of the end 80 of the leaf spring 78 on the arm 1 is, as the abutment face 82 of the end zone 79 on this arm 1, arranged parallel to the face 16 of the arm 1, withdrawn with respect to this face 16 and for example, as is illustrated, coplanarly with the abutment face 82.

However, the abutment face 83 is provided differently on the one hand in the embodiment of FIGS. 1 to 7, and on the other hand in the case of the embodiments of FIGS. 8 to 26.

In the case of the embodiments of FIGS. 8 to 26, the abutment face 83 is defined by a transverse partition 87 rigid with the arm 1, and mutually separating the recesses 56 and 77, close to the projection 50, so that the abutment face 83 is fixed with respect to the arm 1.

On the contrary, in the case of the embodiment of FIGS. 1 to 8, the abutment face 83 is movable longitudinally with respect to the arm 1, while conserving its parallelism of this and its spacing with respect to this face 16, that is to say its coplanarity with the abutment face 82 in the illustrated example.

In effect, in the embodiment of FIGS. 1 to 7, the abutment face 83 of the end 81 of the leaf spring 78 on the arm 1 is defined by a face of a bolt 90 mounted for longitudinal sliding along the arm 1 to be able to occupy with respect to this on the one hand a locking position in which it is illustrated in the Figures, and in which it comes into engagement with a catch constituted in the preferred manner by the projection 50 for immobilising the two arms 1 and 2 against a relative rotation about the axis 7 in their closed positions of the instrument, and on the other hand a position of disengagement with respect to the catch for freeing the two arms 1 and 2 with respect to such a rotation, naturally in the limits permitted by the abutments constituted by the faces 61 and 68 respectively of the edge 57 of the abutment 49 and of the edge 64 of the projection 50.

For this, the bolt 90 is accessible in the manual operation zone 8 of the arm 1, by a control button 91.

More precisely, as appears in FIGS. 1, 4, 5, the longitudinal extension of the recess 56 beyond the projection 50 towards the proximal end 5 of the arm 1 has a plane bottom face 92, parallel to the face 16 of the arm 1 and situated withdrawn with respect to this face 16, as well as with respect to the abutment face 82 of the end zone 79 of the leaf spring 78, and two plane lateral faces 93 and 94, symmetric the one to each other with respect to the plane 13 to which they are parallel being mutually spaced perpendicularly to this plane by an identical distance to the distance perpendicularly separating to this plane the faces 85 and 86, so that the faces 93 and 94 connect the bottom face 92 of the recess 56 to the face 16 of the arm 1 in respective coplanar extensions of the faces 85 and 86 of the recess 76.

Complementarily, the bolt 90 is delimited transversely in addition to by the abutment face 83, by a plane face 95 parallel to the face 83 and applied against the face 92, in sliding contact, and by two plane faces 96 and 97 perpendicular to the faces 83 and 95 and arranged parallel between them, respectively on opposite sides of the plane 13 and symmetrically the one to the other with respect to this, in contact respectively with the lateral face 93 and with the lateral face 94 with the possibility of relative sliding; in a longitudinal direction opposite to the direction 4, the faces 83,95,96,97 of the bolt 90 are connected between themselves by a plane transverse face 98 when, in the direction 4, that is to say towards the projection 50, they are connected between themselves by a transverse plane face 99 carrying in a rigid manner, in longitudinal projection in the direction 4 with respect to them, two longitudinal arms 100 and 101 arranged symmetrically to each other with respect to the plane 13, respectively along the length of the lateral faces 93 and 94 of the recess 56 leaving between themselves an intermediate longitudinal space 202, open in the direction 4 towards the projection 50 for communicating to the bolt the form of a fork when it is viewed in a circumferential direction centered on the axis 7; the two arms 100 and 101 are delimited on the one hand by coplanar extensions of the face 83 and on the other hand, towards the bottom face 92 of the recess 56, by respective plane faces 102 and 103 coplanar and parallel to the face 95 but withdrawn with respect to this latter towards the face 83 in such a way that there is a space respectively between each of these faces 102 and 103 and the face 92 of the recess 56.

Complementarily, as is shown more particularly in FIGS. 4 and 7, the projection 50 is extended respectively on opposite sides of the plane 13, perpendicularly to this, through a distance less than the distance separating from this plane the lateral faces 93 and 94 of the recess 56 and, more precisely, at least equal to the distance separating from this plane the two arms 100 and 101 so that these latter, in the bolted position, are engaged respectively on opposite sides of the projection 50, received in the recess 56 when the arms 1 and 2 occupy their relative position of closure of the instrument; in this position, the projection 50 has along the length of the bottom face 92 of the recess 56 two edges 104 and 105 situated respectively on opposite sides of this projection 50 in a direction parallel to the axis 7, and which are inserted between the bottom face 92 and, respectively, the face 102 of the arm 100 and the face 103 of the arm 101, practically without play; there results the desired bolting of the instrument in its closed position, since the bolt 90 is retained pressed by its face 95 against the bottom face 92 of the recess 56.

For this, the button 91 is arranged essentially opposite the face 14 of the manual operation zone 8, in a symmetric disposition with respect to the plane 13, and it is connected in a rigid manner to the bolt 90 by a neck zone 106 also symmetric with respect to the plane 13, but having perpendicularly to this dimensions less than those of the rest of the button 91 similar to the distance perpendicularly separating at the plane 13 the faces 96 and 97 of the bolt 90; the neck zone 106 crosses the arm 1, from the face 14 of the bottom face 92 of the recess 56, via a longitudinal slot 107 delimited in the direction of extension with respect to the plane 13 by two plane faces 108 and 109, parallel to the plane 13 and arranged symmetrically to each other with respect to this, with a mutual spacing less than the mutual spacing of the faces 96 and 97 of the bolt and at this of the side faces 93 and 94 of the recess 56 similar to the dimensions which the button 91 has perpendicularly to the plane 13 to contact the face 14 of the manual operation zone 8 whilst at the same time being greater than the dimensions of the neck zone 106 perpendicularly to the plane 13; thus, the bolt 90 and the button 91 enclose between them, respectively on one side and the other of the neck zone 106, marginal zones of the slot 107 with the possibility of longitudinal sliding along the length of these zones without the possibility of any other movement.

Longitudinally, the slot 107, the recess 56, and the bolt 90 have respective dimensions such that, by sliding of the neck zone 106 of the button 91 in the slot 107 and sliding of the bolt 90 in the recess 56, one can bring the bolt 90 either into its bolted position in which the arms 100 and 101 fix the projection 50 inside the recess 56 as is illustrated, or into a position in which the fingers 00 and 101 are entirely withdrawn longitudinally with respect to the projection 50 for freeing this latter for a relative rotation of the two arms 1 and 2 of the axis 7 in the direction of mutual spacing of the distal ends 22 and 23 of these arms.

In being applied against the face 83 by its end 80, the leaf spring 78 opposes premature sliding of the bolt 90-button 91 assembly in one direction or the other; preferably, as is illustrated, an immobilisation of the bolt 90 is ensured in the two respectively corresponding positions to the coupling of the arms 100 and 101 with the edges 104 and 105 of the projection 50 and to the freeing of this projection 50; for this, the face 83 has two depressions 110 and 111 arranged so that the leaf spring 78 engages there via its end 80, in a resilient abutment relation in a circumferential direction centered on the axis 7, respectively in one or other of the mentioned positions of the bolt 90.

Naturally, other methods of mutual bolting of the arms 1 and 2 of the instrument according to the present invention can be adopted without departing from the scope of the present invention; however the extremely simple shape will be noted under which have been gathered together, in the embodiment of FIGS. 1 to 8, such means with the means intended to limit the mutual spacing of the distal ends of the arms in the open position of the instrument and means for preventing relative displacement of the distal ends of the arms parallel to the axis of their mutual pivoting.

Similarly, although there has been illustrated and described bolting means for the two arms in the closed position of the instrument exclusively in the case of the embodiment of FIGS. 1 to 8, a man skilled in the art will easily understand that one can provide such means also in the case of the instruments illustrated in FIGS. 10 to 26, at the same time as the instrument illustrated in FIGS. 1 to 8 can be provided without the bolting means.

Having thus described the effective or potential common points in the different instruments illustrated in FIGS. 1 to 26, the specific details of each of these will now be described, that is to say the shape of their respective distal ends, by way of non-limitative examples of microsurgical instruments being able to be made according to the present invention.

In the case of the instrument illustrated in FIGS. 1 to 7, that is to say a needle-holder, the distal ends 22 and 23 of the arms 1 and 2 of the instrument have a generally rectilinear shape in the median direction 112 situated in the plane 12 and deviating from the plane 13 in the direction 4, forming with the plane 13 an angle $\alpha$ for example between 30° and 45°; the distal ends 22 and 23 have in this case a tapered nose shape, presenting to each other respective plane faces 113 and 114 respectively coplanarly extending the faces 34 and 35, that is to say mutually abutting in the closed position of the instrument illustrated particularly in FIG. 2; in a manner known in itself, the faces 113 and 114 can be provided with a recess or bossing facilitating the holding of a curved needle.

The distal ends 24 and 25 of the pincers illustrated in FIGS. 8 and 9 have themselves also a rectilinear shape with a median direction 115 diverging in the direction 4 with respect to the plane 13 forming with respect to this an angle $\beta$ of the order of 30° to 45°, the median direction 115 being also situated in the plane 12 if the instrument is supposed closed; in the case of this instrument, the distal ends 24 and 25 present towards each other respective plane faces 116 and 117 provided without any relief or hollow, extending respectively coplanarly the faces 34 and 35 in a manner to be mutually abutted on the plane 12 when the instrument is closed.

The respective distal ends 26 and 27 of the arms 1 and 2 of the right upper muscle pincers illustrated in FIGS. 10 to 14 also have a generally rectilinear shape on a median direction 118 diverging in the direction 4 with respect to the plane 13, forming at the same time with respect to this an angle $\gamma$ between 45° and 60°; the instrument being considered in the closed state, the median direction 118 is also situated in the plane 12 along which the distal ends 26 and 27 are abutted by respective plane faces 119 and 120 respectively coplanarly extending the faces 34 and 35; however, in the case of this embodiment of an instrument according to the present invention, and as appears more particularly from examining FIGS. 13 to 14, the respective distal ends 26 and 27 of the arms 1 and 2 have at their ends, in respective circumferential directions centered on the axis 7, respectively two claws 121 projecting on the face 119 and perpendicularly juxtaposed to the direction 118, and a claw 122 projecting on the face 120, which claw 122 is received between the two claws 121 when the pincers are in a closed state but which is totally disengaged from the claws 121 when the pincers are in the open state.

The respective distal ends 28 and 29 of the arms 1 and 2 of the claw pincers illustrated in FIGS. 15 to 18 have themselves a median longitudinal direction, with a rectilinear tapered shape in the longitudinal direction 4; when the pincers are in a closed state, the distal ends 28 and 29 are in mutual contact, on the plane 12, via respective faces 123 and 124 respectively coplanarly extending the faces 34 and 35; as appears better in FIGS. 17 and 18, the face 123 has in projection, at its end, a claw 125 arranged in the plane 13 whilst the face 124 has in projection, at its end, two claws 126 arranged symmetrically to each other with respect to the plane 13 for being placed respectively on opposite sides of the claw 125 when the pincers are in a closed state; when the pincers are in the open state, the claws 126 disengage totally from the claw 125.

In the case of these different instruments, illustrated in FIGS. 1 to 18, the distal ends of the arms constitute consequently noses able to co-operate in a pinching action by mutual contact in a circumferential direction centered on the axis 7 and, possibly, mutual overlapping of claws due to a relative rotation of the arms tending to close the instrument.

The two embodiments shown in FIGS. 19 to 26 correspond themselves to cases in which distal ends of the arms have the form of blades able to co-operate in a cutting action by mutual crossing in such a circumferential direction and mutual contact in a direction parallel to the axis 7 due to a relative rotation of the arms 1 and 2 in the direction of closure of the instrument.

More precisely, in the case of the embodiment illustrated in FIGS. 19 to 22, the distal ends 30 and 31 of the arms 1 and 2 are tightly juxtaposed in a direction parallel to the axis 7 (not visible in these Figures) when the instrument is in the closed state; then, they are directed in a common median direction 127 which, when the instrument is seen perpendicularly to the plane 13 as is the case in FIG. 21, appears rectilinear and diverges with respect to the plane 12 in the direction 4, from the same side of this plane 12 as the arm 1 in forming with respect to the plane 12 an angle $\delta$ for example of the order of 30°; on the contrary, when the instrument is seen perpendicularly to the plane 12 as is the case in FIG. 20 or again longitudinally as is the case in FIG. 22, the distal ends 30 and 31 juxtaposed in a direction parallel to the axis 7 when the instrument is closed have a curvilinear median direction, progressively diverging from the plane 13, from the side of this corresponding to the distal end 31 of the arm 2.

In this case, for permitting relative pivotal movements of the two arms 1 and 2 about the axis 1, the distal ends 30 and 31 present towards each other respective faces 128 and 129 defined by respective circular generatrices, centered on the axis 7 when, the instrument being supposed to be in the open state as is partially shown in FIG. 21, these distal ends 30 and 31 present towards each other respective opposite cutting edges 130 and 131 oriented in circumferential directions centered on the axis 7 and in opposed manner on these circumferential directions.

The determination of the precise geometry of the faces 128 and 129 and the cutting edges 130 and 131 of the respective distal ends 30 and 31 of the arms 1 and 2 of the instrument illustrated in FIGS. 19 to 22 is in the domain of the normal abilities of the man skilled in the art, knowing particularly the distance separating these faces or cutting edges with respect to the axis 7 of mutual pivoting of the two arms and the shape of incisions to be made by means of the scissors.

The FIGS. 23 to 26 illustrate another type of scissors, in which the respective distal ends 32 and 33 are arranged, when the instrument is closed, in the same median direction situated in the plane 12 but progressively diverging with respect to the plane 13 in the direction 4, from the side of the distal end 32 of the arm 1, with a curvilinear shape; when the scissors are in the closed state, the distal zones 32 and 33 in the form of blades are juxtaposed parallel to the axis 7 by respective faces 132,133 defined by circumferential generatrices centered on the axis 7 whilst, when the arms 1 and 2 are in an open position of the scissors, these distal ends in the form of blades 32 and 33 present towards each other, in circumferential directions centered on the axis 7, respective cutting edges 134 and 135; in this case also, the determination of the respective shapes 132 and 133 and of the cutting edges 134 and 135 is in the domain of the normal abilities of the man skilled in the art.

As has been said above, the embodiments of the present invention which have been described are in no way limitative and, in particular, one can orient differently the noses or blades constituting the respective distal ends of the instruments which have been described, for example for providing a pincers for the left upper muscle from the pincers described with reference to FIGS. 11 to 14, or right cornea grafting scissors from the scissors described with reference to FIGS. 19 to 22.

I claim:

1. A microsurgical instrument for use as pincers or scissors, said microsurgical instrument comprising:
two rigid longitudinal arms mutually pivoted about a defined transverse axis and have on one hand respective proximal ends and on the other hand respective distal ends, said distal ends being longitudinally spaced with respect to said axis and adapted to co-operate in a pinching or cutting action, respectively, by relative rotation of the two arms about said axis in a first direction corresponding to a mutual approach of said distal ends, the arms having respective manual operation zones for relative rotation about said axis in said first direction whilst there is provided means for resilient urging of the arms into relative rotation about said axis in a second direction opposite to said first direction and corresponding to a mutual spacing of said distal ends,
said axis being situated at the proximal ends of the arms, and said manual operation zones being situated between said axis and the distal ends of the arms,
both of the arms have in a fixed manner, at their proximal ends, at least one respective longitudinal lug arranged side to side, and said at least one respective longitudinal lug being pierced on said axis with respective bores in which is engaged a common pivot pin.

2. A microsurgical instrument according to claim 1, characterised in that it comprises means for limiting mutual spacing of the distal ends of the arms.

3. A microsurgical instrument according to claim 2, characterised in that the means for limiting mutual spacing of the distal ends of the arms comprise at least two abutment surfaces respectively fixed in the arms and situated at said proximal ends, approximately transversely, opposite each other in a circumferential direction centered on said axis and in a relative position such that they mutually approach or are spaced from each other, when, respectively, said distal ends mutually move apart or approach.

4. A microsurgical instrument according to claim 2, characterised in that the means for limiting mutual spacing of the distal ends of the arms comprise at least two abutment surfaces respectively fixed in the arms and situated between said axis and said distal ends, opposite each other in a circumferential direction centered on said axis and in a relative position such that they mutually approach or move apart from each other when, respectively said distal ends are mutually moved apart or together.

5. A microsurgical instrument according to claim 4, characterised in that said abutment surfaces situated between said axis and said distal ends are closer to said distal ends than said axis and approximately longitudinal.

6. A microsurgical instrument according to claim 4, characterised in that it comprises means for mutual guiding of the arms in relative rotation about said axis without possibility of relative translation parallel to said axis.

7. A microsurgical instrument according to claim 6, characterised in that the means for mutual guiding of the arms comprise at least two abutment surfaces fixed in one of the arms and situated at said proximal end of this, perpendicular to said axis and in opposed orientations, and at least two counterpart surfaces fixed in the other arm and situated at said proximal end of this, perpendicularly to said axis and opposite, parallel to this axis, respectively with each other abutment surfaces with which said counterpart surfaces are respectively in contact with the possibility of mutual sliding.

8. A microsurgical instrument according to claim 6, characterised in that the means for mutual guiding of the arms comprise at least two abutment surfaces fixed in one of the arms and situated between said axis and said distal ends, perpendicularly to said axis and in opposed orientations, and at least two counterpart surfaces fixed in the other arm and situated between said axis and said distal ends, perpendicularly to said axis and opposite, parallel to this axis, respectively with each other abutment surfaces with which said counterpart surfaces are respectively in contact with the possibility of mutual sliding.

9. A microsurgical instrument according to claim 8, characterised in that said surfaces respectively of abutment and counterpart situated between said axis and said distal ends are closer to said distal ends than said axis.

10. A microsurgical instrument according to claim 8, characterised in that the two arms have opposite each other in respective circumferential directions centered on said axis, in a fixed manner, between said axis and said distal ends, respective transverse projections arranged in the same median plane perpendicular to said axis and spaced longitudinally with respect to each other, in that the projection of each arm has towards the projection of the other arm an edge approximately longitudinal defining on the one hand said abutment surface and on the other hand, respectively, said abutment surfaces or said counterpart surfaces.

11. A microsurgical instrument according to claim 10, characterised in that each arm has a recess opposite the projection of the other arm in a circumferential direction, centered on said axis, for freely receiving this projection.

12. A microsurgical instrument according to claim 10, characterised in that is comprises means for immobilization, at will, of the two arms against a relative rotation about said axis in said second direction, in a relative position of maximum mutual approach of said distal ends.

13. A microsurgical instrument according to claim 12, characterised in that said immobilization means comprise between said axis and said distal ends, on the one hand a catch rigid with one of the arms and on the other hand a bolt mounted for longitudinal sliding on the other arm and manually accessible in the manual operation zone of this arm for being driven at will into a position of engagement with the catch, for bringing about the said immobilization, or into a position of disengagement with respect to the catch, for removing said immobilization.

14. A microsurgical instrument according to claim 13, characterised in that the bolt is situated between said axis and the catch.

15. A microsurgical instrument according to claim 13, characterised in that said catch is constituted by one of said projections.

16. A microsurgical instrument according claim 15, characterised in that the bolt has perpendicularly to a circumferential direction centered on said axis and towards said projection forming the catch the shape of a longitudinal fork able to be engaged on opposite sides of said projection forming the catch, and in that said projection forming the catch has two edges respectively situated on opposite sides in a direction parallel to said axis, for cooperating with the fork in said position of mutual engagement of the bolt and the catch.

17. A microsurgical instrument according to claim 13, characterised in that it comprises means for immobilization of the bolt against accidental longitudinal sliding.

18. A microsurgical instrument according to claim 17, characterised in that the leaf spring is in abutment via the intermediary of the bolt on the arm on which the bolt is mounted for longitudinal sliding.

19. A microsurgical instrument according to claim 18, characterised in that the bolt has opposite the spring a flat abutment face, approximately longitudinal and perpendicular to a circumferential direction centered on said axis, said plane abutment face having two depressions able to receive abutment of the spring respectively in said position of mutual engagement of the bolt and the catch and in said position of mutual disengagement of the bolt and the catch.

20. A microsurgical instrument according to claim 10, characterised in that the resilient urging means comprise at least one compression spring interposed between the arms, between said axis and the said distal ends.

21. A microsurgical instrument according to claim 20, characterised in that the resilient urging means comprise at least one approximately longitudinal leaf spring, curved in a median plane perpendicular to the axis, and having two end zones in abutment against one of the arms in respective circumferential directions centered on said axis and an intermediate zone in abutment against the other arm in a circumferential direction centered on said axis, between said axis and said distal ends.

22. A microsurgical instrument according to claim 21, characterised in that the leaf spring is situated between said axis and said transverse projections of the arms.

23. A microsurgical instrument according to claim 1, characterised in that said distal ends have the form of noses able to co-operate in a pinching action by mutual contact in a circumferential direction centered on said axis due to a relative rotation of the arms in said first direction.

24. A microsurgical instrument according to claim 23, characterised in that said noses have opposite each other in respective circumferential directions centered on said axis respective claws able to mate as a result of a relative rotation of the arms in said first direction.

25. A microsurgical instrument according to claim 1, characterised in that said distal arms have the form of blades able to co-operate in a cutting action by mutual crossing in a circumferential direction centered on said axis and in mutual contact in a direction parallel to said axis due to a relative rotation of the arms in said first direction, said blades having for this opposed respective cutting edges oriented in circumferential directions centered on said axis.

26. A microsurgical instrument according to claim 1, characterised in that said distal ends are curved with respect to a plane including said axis.

27. A microsurgical instrument according to claim 1, characterised in that said distal ends are curved with respect to a plane perpendicular to said axis.

28. A microsurgical instrument according to claim 1, characterised in that said distal ends are arranged in a plane including said axis.

29. A microsurgical instrument according to claim 1, characterized in that said distal ends are arranged in a plane perpendicular to said axis.

30. A microsurgical instrument for use as pincers or scissors, said microsurgical instrument comprising:
two rigid longitudinal arms which are mutually pivoted about a defined transverse axis and have on the one hand respective proximal ends and on the other hand respective distal ends, said distal ends being longitudinally spaced with respect to said axis and adapted to co-operate in a pinching or cutting action, respectively, by relative rotation of the two arms about said axis in a first direction corresponding to a mutual approach of said distal ends, the arms having respective manual operation zones for relative rotation about said axis in said first direction whilst there is provided means for resilient urging of the arms into relative rotation about said axis in a second direction opposite to said first direction and corresponding to a mutual spacing of said distal ends,
said axis being situated at the proximal ends of the arms, and said manual operation zones being situated between said axis and the distal ends of the arms,
one of the arms has in a fixed manner, at its proximal end, at least one longitudinal lug arranged on a median plane perpendicular to said axis whilst the other arm has in a fixed manner, at its proximal end at least two longitudinal lugs arranged on respective median planes perpendicular to said axis, respectively on opposite sides of the mentioned longitudinal lug, and in that said longitudinal lugs are pierced on said axis with respective bores in which is engaged a common pivot pin.

31. A microsurgical instrument for use as pincers or scissors, said microsurgical instrument comprising:

two rigid longitudinal arms which are mutually pivoted about a defined transverse axis and have on the one hand respective proximal ends and on the other hand respective distal ends, said distal ends being longitudinally spaced with respect to said axis and adapted to co-operate in a pinching or cutting action, respectively, by relative rotation of the two arms about said axis in a first direction corresponding to a mutual approach of said distal ends, the arms having respective manual operation zones for relative rotation about said axis in said first direction whilst there is provided means for resilient urging of the arms into relative rotation about said axis in a second direction opposite to said first direction and corresponding to a mutual spacing of said distal ends, said axis being situated at the proximal ends of the arms, said manual operation zones being situated between said axis and the distal ends of the arms, means for limiting mutual spacing of the distal ends of the arms, said means for limiting mutual spacing of the distal ends of the arms includes at least two abutment surfaces respectively fixed in the arms and situated at said proximal ends, approximately transversely, opposite each other in a circumferential direction centered on said axis and in a relative position such that they mutually approach or are spaced from each other, when, respectively, said distal ends mutually move apart or approach.

32. A microsurgical instrument for use as pincers or scissors, said microsurgical instrument comprising:

two rigid longitudinal arms which are mutually pivoted about a defined transverse axis and have on the one hand respective proximal ends and on the other hand respective distal ends, said distal ends being longitudinally spaced with respect to said axis and adapted to co-operate in a pinching or cutting action, respectively, by relative rotation of the two arms about said axis in a first direction corresponding to a mutual approach of said distal ends, the arms having respective manual operation zones for relative rotation about said axis in said first direction whilst there is provided means for resilient urging of the arms into relative rotation about said axis in a second direction opposite to said first direction and corresponding to a mutual spacing of said distal ends, said axis being situated at the proximal ends of the arms, said manual operation zones being situated between said axis and the distal ends of the arms, means for limiting mutual spacing of the distal ends of the arms, said means for limiting mutual spacing of the distal ends of the arms includes at least two abutment surfaces respectively fixed in the arms and situated between said axis and said distal ends, opposite each other in a circumferential direction centered on said axis and in a relative position such that they mutually approach or are spaced from each other when, respectively said distal ends are mutually moved apart or together.

33. A microsurgical instrument for use as pincers or scissors, said microsurgical instrument comprising:

two rigid longitudinal arms which are mutually pivoted about a defined transverse axis and have on the one hand respective proximal ends and on the other hand respective distal ends, said distal ends being longitudinally spaced with respect to said axis and adapted to co-operate in a pinching or cutting action, respectively, by relative rotation of the two arms about said axis in a first direction corresponding to a mutual approach of said distal ends, the arms having respective manual operation zones for relative rotation about said axis in said first direction whilst there is provided means for resilient urging of the arms into relative rotation about said axis in a second direction opposite to said first direction and corresponding to a mutual spacing of said distal ends, said axis being situated at the proximal ends of the arms, said manual operation zones being situated between said axis and the distal ends of the arms, said distal ends having the form of noses able to co-operate in a pinching action by mutual contact in a circumferential direction centered on said axis due to a relative rotation of the arms in said first direction.

* * * * *